US00PP27285P2

(12) United States Plant Patent
van Huylenbroeck

(10) Patent No.: US PP27,285 P2
(45) Date of Patent: Oct. 18, 2016

(54) ***HIBISCUS* PLANT NAMED 'ILVO347'**

(50) Latin Name: *Hibiscus syriacus*
Varietal Denomination: ILVO347

(71) Applicant: Johan van Huylenbroeck, Melle (BE)

(72) Inventor: Johan van Huylenbroeck, Melle (BE)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 14/545,048

(22) Filed: Mar. 19, 2015

(51) Int. Cl.
*A01H 5/02* (2006.01)

(52) U.S. Cl.
USPC ..... Plt./257

(58) Field of Classification Search
USPC ..... Plt./257
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Hibiscus* plant named 'ILVO347', characterized by its upright and outwardly spreading plant habit; vigorous growth habit; freely branching habit; freely flowering habit; large sterile orchid pink-colored flowers with dark red-colored centers; and good garden performance.

3 Drawing Sheets

Botanical designation: *Hibiscus syriacus*.
Cultivar denomination: 'ILVO347'.

BACKGROUND OF THE INVENTION

The present invention relates to a new and distinct cultivar of *Hibiscus* plant, botanically known as *Hibiscus syriacus*, commercially known as Rose-of-Sharon or Althea, and hereinafter referred to by the cultivar name 'ILVO347'.

The new *Hibiscus* plant is a product of a planned breeding program conducted by the Inventor in Melle, Belgium. The objective of the breeding program was to develop new sterile *Hibiscus* plants with uniform plant habit and unique flower coloration.

The new *Hibiscus* plant originated from a cross-pollination in 2000 of an unnamed proprietary selection of *Hibiscus syriacus*, not patented, as the female, or seed, parent with *Hibiscus syriacus* 'Red Heart', not patented, as the male, or pollen, parent. The new *Hibiscus* plant was discovered and selected by the Inventor in 2003 as a flowering plant within the progeny of the stated cross-pollination in a controlled environment in Melle, Belgium.

Asexual reproduction of the new *Hibiscus* plant by softwood cuttings in a controlled greenhouse environment in Melle, Belgium since 2003 has shown that the unique features of this new *Hibiscus* plant are stable and reproduced true to type in successive generations of asexual reproduction.

SUMMARY OF THE INVENTION

Plants of the new *Hibiscus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'ILVO347'. These characteristics in combination distinguish 'ILVO347' as a new and distinct *Hibiscus* plant:

1. Upright and outwardly spreading plant habit.
2. Vigorous growth habit.
3. Freely branching habit.
4. Freely flowering habit.
5. Large sterile orchid pink-colored flowers with dark red-colored centers.
6. Good garden performance.

Plants of the new *Hibiscus* can be compared to plants of the female parent selection. Plants of the new *Hibiscus* differ primarily from plants of the female parent selection in flower color as plants of the female parent selection have white-colored flowers.

Plants of the new *Hibiscus* can be compared to plants of the male parent, 'Red Heart'. Plants of the new *Hibiscus* differ primarily from plants of 'Red Heart' in flower color as plants of 'Red Heart' have white-colored flowers with red-colored centers. In addition, flowers of plants of the new *Hibiscus* are sterile whereas flowers of plants of 'Red Heart' are fertile and produce seeds.

Plants of the new *Hibiscus* can also be compared to plants of the *Hibiscus syriacus* 'Minrosa', disclosed in U.S. Plant patent application Ser. No. 09/642,987 (abandoned). In side-by-side comparisons conducted in Melle, Belgium, plants of the new *Hibiscus* differed primarily from plants of 'Minrosa' in flower color as plants of 'Minrosa' had pink-colored flowers with red-colored centers. In addition, flowers of plants of the new *Hibiscus* were sterile whereas flowers of plants of 'Minrosa' were fertile and produced seeds.

BRIEF DESCRIPTION OF THE PHOTOGRAPHS

The accompanying colored photographs illustrate the overall appearance of the new *Hibiscus* plant showing the colors as true as it is reasonably possible to obtain in colored reproductions of this type. Colors in the photographs may differ slightly from the color values cited in the detailed botanical description which accurately describe the colors of the new *Hibiscus* plant.

The photograph on the first sheet is a side perspective view of a typical flowering plant of 'ILVO347' grown in a container.

The photograph on the second sheet is a side perspective view of a typical flowering plant of 'ILVO347' grown in a ground bed.

The photograph on the third sheet is a close-up view of a typical open flower and flower buds of 'ILVO347'.

DETAILED BOTANICAL DESCRIPTION

The aforementioned photographs and following observations, measurements and values describe plants grown in one-gallon containers and in ground beds in Grand Haven, Mich. during the summer in a polypropylene-covered shadehouse and under cultural practices typical of commercial *Hibiscus* production. During the production of the plants, day temperatures ranged from 18° C. to 27° C. and night temperatures ranged from ranged from 5° C. to 10° C. Plants were one year old when the description was taken. In the description, color references are made to The Royal Horticultural Society Colour Chart, 1995 Edition, except where general terms of ordinary dictionary significance are used.

Botanical classification: *Hibiscus syriacus* 'ILVO347'.

Parentage:

*Female, or seed, parent*.—Unnamed proprietary selection of *Hibiscus syriacus*, not patented.

*Male, or pollen, parent*.—*Hibiscus syriacus* 'Red Heart', not patented.

Propagation:

*Type*.—By softwood cuttings.

*Time to initiate roots, summer*.—About 20 days at temperatures about 25° C.

*Time to produce a rooted young plant, summer*.—About three months at temperatures about 25° C.

*Root description*.—Fine to thick; fibrous.

*Rooting habit*.—Freely branching; dense.

Plant description:

*Plant and growth habit*.—Perennial shrub; upright and outwardly spreading plant habit; vigorous growth habit.

*Branching habit*.—Freely branching habit with typically five primary and numerous secondary lateral branches developing per plant; pinching enhances lateral branch development.

*Plant height*.—About 70 cm.

*Plant diameter* (*area of spread*).—About 76.5 cm.

Lateral branch description:

*Length*.—About 20 cm.

*Diameter*.—About 3 mm.

*Internode length*.—About 3.5 cm.

*Aspect*.—About 25° to 50° from vertical.

*Strength*.—Strong, rigid.

*Texture, immature*.—Pubescent.

*Texture, mature*.—Woody.

*Color, immature*.—Close to 148B.

*Color, mature*.—Close to 197B.

Leaf description:

*Arrangement*.—Mostly alternate, simple.

*Length*.—About 11.1 cm.

*Width*.—About 6.1 cm.

*Shape*.—Ovate.

*Apex*.—Acute.

*Base*.—Cuneate.

*Margin*.—Crenate; lobed.

*Texture, upper surface*.—Smooth, glabrous; waxy.

*Texture, lower surface*.—Slightly pubescent; waxy.

*Venation pattern*.—Palmate.

*Color*.—Developing leaves, upper surface: Close to 141A. Developing leaves, lower surface: Close to 143A. Fully expanded leaves, upper surface: Close to 139A; venation, close to 137C. Fully expanded leaves, lower surface: Close to 137B; venation, close to 146C.

*Petioles*.—Length: About 2.7 cm. Diameter: About 3 mm. Texture, upper surface: Pubescent. Texture, lower surface: Smooth, glabrous. Color, upper and lower surfaces: Close to 138A.

Flower description:

*Flower appearance and arrangement*.—Large single rotate flowers; flowers, terminal and axillary; freely flowering habit with usually about 13 flowers developing per lateral branch; flowers face upright to mostly outwardly.

*Flower longevity*.—Flowers last about two to three days on the plant; flowers not persistent.

*Natural flowering season*.—Plants typically flower during the mid to late summer in Michigan.

*Fragrance*.—None detected.

*Flower diameter*.—About 8.1 cm.

*Flower length* (*height*).—About 7 cm.

*Flower buds*.—Length: About 1 cm. Diameter: About 1 cm. Shape: Ovoid. Color: Close to 138B.

*Petals*.—Arrangement and quantity: Single whorl of five petals; petals slightly imbricate. Length: About 6.5 cm. Width: About 2.8 cm. Shape: Obovate. Apex: Broadly obtuse, rounded. Base: Cuneate. Margin: Entire; sinuate. Texture, upper and lower surfaces: Smooth, glabrous; silky. Color: When opening, upper surface: Close to 76B; center and towards the base, close to 59A. When opening, lower surface: Close to 75C; center slightly tinted with close to 61A. Fully opened, upper surface: Close to between 76A and 95D; center and towards the base, close to 59A; venation, similar to petal surface colors; colors do not fade with development. Fully opened, lower surface: Close to between 76B and 95D; center and towards the base, close to 59A; venation, similar to petal surface colors; colors do not fade with development.

*Sepals*.—Arrangement and quantity: Six to seven in a single whorl. Length: About 2.1 cm. Width: About 2 cm. Shape: Narrowly deltoid. Apex: Narrowly acute. Base: Truncate. Margin: Entire. Texture, upper surface: Slightly pubescent. Texture, lower surface: Smooth, glabrous. Color, immature and mature, upper surface: Close to 139A. Color, immature and mature, lower surface: Close to 137A.

*Peduncles*.—Length: About 2.7 cm. Diameter: About 3 mm. Aspect: Erect to about 50° from the stem axis. Strength: Strong, flexible. Texture: Slightly pubescent. Color: Close to 141B.

*Reproductive organs*.—Androecium: Quantity of stamens per flower: About 40. Filament length: About 3 mm. Filament color: Close to 155C. Anther shape: Globular. Anther length: About 2 mm. Anther color: Close to 155C. Amount of pollen: Abundant. Pollen color: Close to 10D. Gynoecium: Quantity of pistils per flower: One. Pistil length: About 4.9 cm. Style length: About 4.5 cm. Style color: Close to 155C. Stigma appearance: Five-parted, globular. Stigma color: Close to 155C. Ovary color: Close to 155C overlain with close to 145A and 145B.

*Seeds and fruits*.—Flowers of plants of the new *Hibiscus* are sterile and seed and fruit development have not been observed.

Garden performance: Plants of the new *Hibiscus* have been observed to have good garden performance and to tolerate rain, wind, drought and temperatures ranging from about −20 C to about 43° C.

Pathogen & pest resistance: Plants of the new *Hibiscus* have not been shown to be resistant to pathogens and pests common to *Hibiscus* plants.

It is claimed:

1. A new and distinct *Hibiscus* plant named 'ILVO347' as illustrated and described.

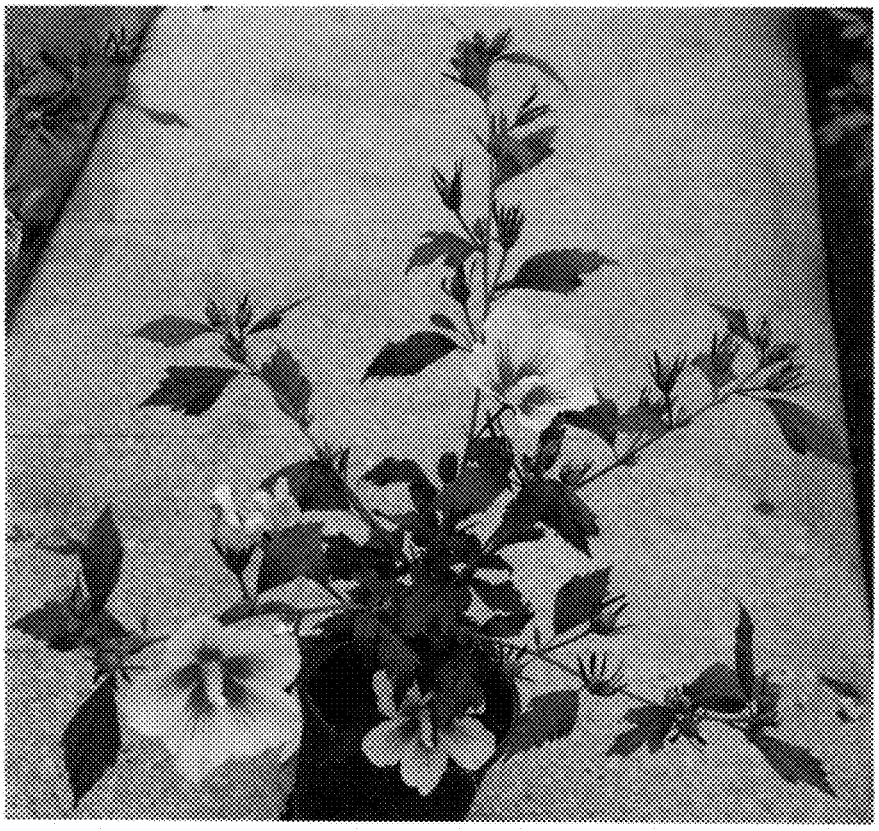

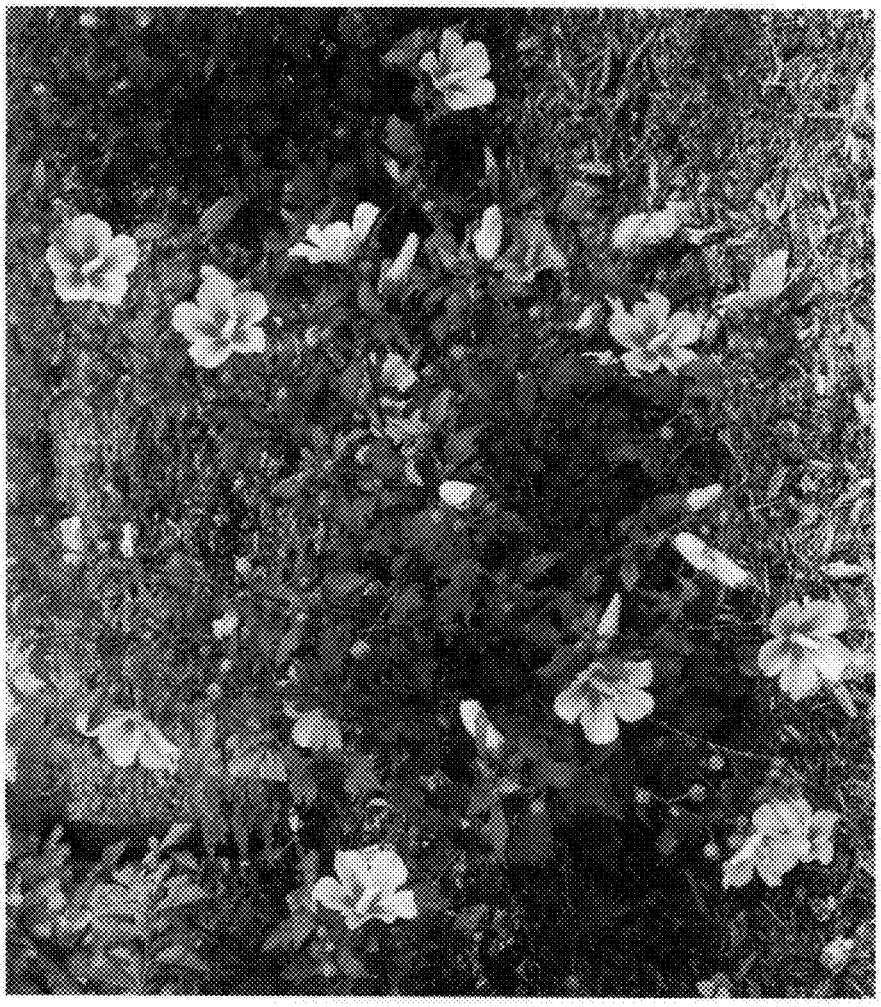

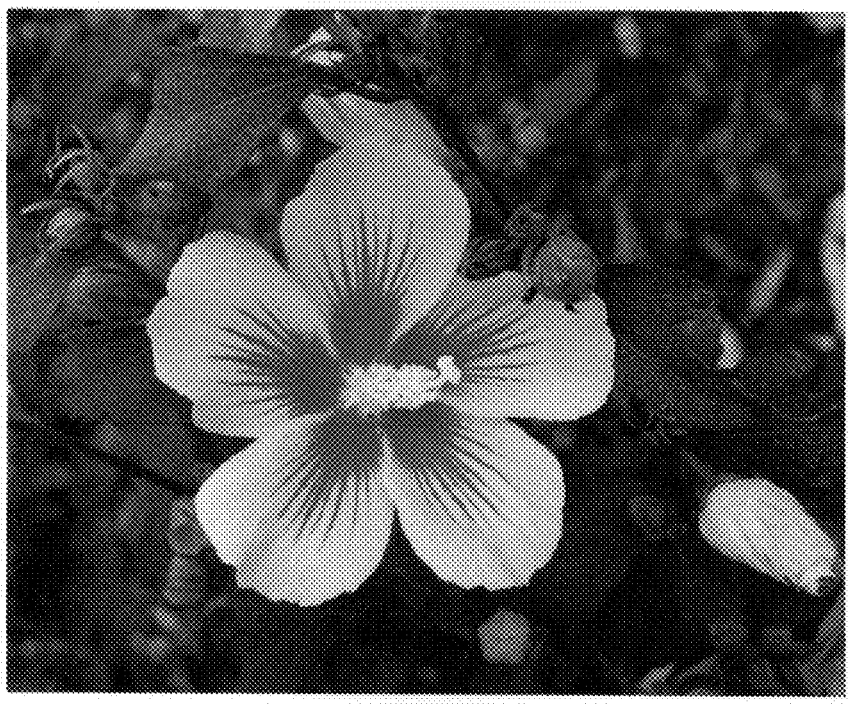

* * * * *